United States Patent [19]

Machhammer et al.

[11] Patent Number: 5,817,865
[45] Date of Patent: Oct. 6, 1998

[54] PREPARATION OF ACRYLIC ACID AND ESTERS

[75] Inventors: Otto Machhammer, Mannheim; Toni Dockner, Meckenheim; Gerd-Jürgen Engert, Ludwigshafen; Theo Proll, Bad Dürkheim, all of Germany

[73] Assignee: BASF Aktiengesellschaft, Ludwigshafen, Germany

[21] Appl. No.: 779,235

[22] Filed: Jan. 3, 1997

[30] Foreign Application Priority Data

Jan. 12, 1996 [DE] Germany .................. 196 00 955.3

[51] Int. Cl.⁶ .......................... C07C 67/00; C07C 51/16
[52] U.S. Cl. .................. 560/208; 562/512.2; 562/532
[58] Field of Search .................. 560/208; 562/512.2, 562/532

[56] References Cited

U.S. PATENT DOCUMENTS

| | | |
|---|---|---|
| 3,198,750 | 8/1965 | Callahan et al. . |
| 3,251,899 | 5/1966 | Callahan et al. . |
| 3,437,690 | 4/1969 | Young et al. . |
| 3,725,208 | 4/1973 | Maezawa et al. . |
| 3,736,355 | 5/1973 | Croci et al. . |
| 3,865,873 | 2/1975 | Oda et al. . |
| 3,932,500 | 1/1976 | Duembgen et al. . |
| 3,962,074 | 6/1976 | Schropp . |
| 4,110,370 | 8/1978 | Engelbach et al. . |
| 4,267,386 | 5/1981 | Vanderspurt . |
| 5,426,221 | 6/1995 | Willersinn . |

FOREIGN PATENT DOCUMENTS

| | | |
|---|---|---|
| 3 429 391 | of 0000 | European Pat. Off. . |
| 0 117 146 | 8/1984 | European Pat. Off. . |
| 0 253 409 | 1/1988 | European Pat. Off. . |
| 0 257 565 | 3/1988 | European Pat. Off. . |
| 0 293 224 | 11/1988 | European Pat. Off. . |
| 0 616 998 | 9/1994 | European Pat. Off. . |
| 1 205 502 | 6/1966 | Germany . |
| 1 962 431 | 6/1970 | Germany . |
| 2 164 767 | 7/1972 | Germany . |
| 2 136 396 | 2/1973 | Germany . |
| 2 251 364 | 5/1973 | Germany . |
| 24 49 780 | 4/1976 | Germany . |
| 29 43 707 | 5/1980 | Germany . |
| 43 08 087 | 9/1994 | Germany . |
| 1 450 986 | 9/1976 | United Kingdom . |
| 2 146 636 | 4/1985 | United Kingdom . |

OTHER PUBLICATIONS

Chemical Abstracts, PT 078 759, Jan. 31, 1985.
Chemical Abstracts, JP 48–091 013, Nov. 27, 1973.
Chemical Abstracts, JP 58–140 039, Aug. 19, 1983.
Chemical Abstracts, PT 81 876, Jul. 17, 1986.
Derwent Abstracts, AN 88–030135/05, JP 01 124 766, May 17, 1989.
Derwent Abstracts, AN 95–204248/27, JP 07 118 766, May 9, 1995.
Derwent Abstracts, AN 93–220872/28, EP 551 111, Jul. 14, 1993.
Derwent Abstracts, AN 88–163034/24, EP 270999, Jun. 15, 1988.
Chemical Abstracts, JP 71–18 966, May 27, 1971.
Chemical Abstracts, JP 71–189 68, May 27, 1971.
Chemical Abstracts, JP 72–418 85, Oct. 23, 1972.

*Primary Examiner*—Paul J. Killos
*Attorney, Agent, or Firm*—Oblon, Spivak, McClelland, Maier & Neustadt, P.C.

[57] ABSTRACT

A process for preparing acrylic acid and/or esters comprises the steps of:

(a) catalytic gas phase oxidation of propene and/or acrolein to acrylic acid to obtain a gaseous reaction product comprising acrylic acid, (b) solvent absorption of the reaction product, (c) distillation of the solvent loaded with acrylic acid to obtain a crude acrylic acid and the solvent, (d) purification of the crude acrylic acid by crystallization and (e) optionally esterification of the crystalline acrylic acid.

7 Claims, 2 Drawing Sheets

PREPARATION OF ACRYLIC ACID AND ESTERS

The present invention relates to a process and apparatus for preparing acrylic acid and esters.

Acrylic acid is an important basic chemical. Owing to its very reactive double bond and the acid function, it is suitable in particular for use as monomer for preparing polymers. Of the amount of acrylic acid monomer produced, the major part is esterified before polymerization, for example to form acrylate adhesives, dispersions or coatings. Only the smaller part of the acrylic acid monomer produced is polymerized directly, for example to form superabsorbents. Whereas, in general, the direct polymerization of acrylic acid requires high purity monomer, the acrylic acid for conversion into acrylate before polymerization does not have to be so pure.

It is common knowledge that acrylic acid can be produced by heterogeneously catalyzed gas phase oxidation of propene with molecular oxygen over solid catalysts at temperatures between 200° to 400° C. in two stages via acrolein (cf. for example DE-A 19 62 431, DE-A 29 43 707, DE-C 1 205 502, EP-A 257 565, EP-A 253 409, DE-B 22 51 364, EPA 117 146, GB-C 1 450 986 and EP-A 293 224). The catalysts used are oxidic multicomponent catalysts based for example on oxides of the elements molybdenum, chromium, vanadium or tellurium.

DE-C 21 36 396 discloses removing acrylic acid from the reaction gases obtained in the catalytic oxidation of propene or acrolein by a countercurrent absorption with a mixture of 75% by weight diphenyl ether and 25% by weight diphenyl. Furthermore, DT-A 24 49 7800 discloses cooling the hot reaction gas by partly evaporating the solvent in a direct condenser (quench apparatus) ahead of the countercurrent absorption. The problem here and with further process steps is the production of solids in the apparatus, which reduces plant availability. According to DE-A 43 08 087, the amount of these solids can be reduced by adding to the relatively apolar solvent mixture of diphenyl ether and diphenyl a polar solvent, such as dimethyl phthalate, in an amount of from 0.1 to 25% by weight.

Apart from the above-described absorption of the reaction product comprising acrylic acid into a high boiling solvent mixture, other existing processes involve a total condensation of acrylic acid and of the water of reaction also formed in the course of the catalytic oxidation. The result is an aqueous acrylic acid solution which can be further worked up by distillation with an azeotropic agent (cf. DE-C 34 29 391, JA 11 24 766, JA 71 18 766, JA 71 18 966-R, JA 71 18968-R, JA-72 41 885) or by an extraction process (cf. DE-A 2 164 767, J5 81 40-039, J4 80 91 013). In EP-A 551 111, the mixture of acrylic acid and byproducts from the catalytic gas phase oxidation is contacted with water in an absorption tower and the resulting aqueous solution is distilled in the presence of a solvent which forms an azeotrope with polar low boilers such as water or acetic acid. DE-C 23 23 328 describes the removal of acrylic acid from an aqueous acrylic acid esterification waste liquor or an aqueous acrylic acid solution as formed in acrylic acid production by oxidation of propene or acrolein by extraction with a specific mixture of organic solvents.

Regardless of the type of the acrylic acid production processes described above, the quality of acrylic acid obtainable thereby is generally not sufficient to be able to polymerize saleable products therefrom. Any further processing into polyacrylic acid is hampered in particular by the catalytic gas phase oxidation byproducts of acetic acid, propionic acid and aldehydes. It is known to remove aldehydes by chemical pretreatment with AGHC (aminoguanidine hydrogen carbonate) or $NH_2NH_2$ (cf. for example EP-A 270 999, PT-78 759-A, PT 81 876-A, U.S. Pat. No. 3,725,208-S) and further distillative workup steps (low boiler distillation and acrylic acid purification). Acrylic acid purified in this way is suitable for example for preparing superabsorbents. It is also known to remove acetic acid from the acrylates after the esterification by distillation.

Even if the acrylic acid is not used as a direct starting material for the production of polyacrylic acid, but is esterified before further processing, which is true of the bun of the world's crude acid production, the abovementioned cocomponents acetic acid, propionic acid and aldehydes interfere.

Thus, in virtually all further processing options for acrylic acid the same cocomponents, namely acetic acid, propionic acid and aldehydes, interfere. A distillation of acrylic acid is problematical on account of the high temperature stress and the associated strong tendency for the acrylic acid to form dimers, oligomers or polymers. Nor can cocomponents with a similar boiling point, especially propionic acid, be separated off in the distillation of acrylic acid (boiling point of acrylic acid 141.6° C., boiling point of propionic acid 140.9° C.).

It is an object of the present invention to provide a process for preparing acrylic acid or esters whereby the abovementioned interfering secondary components are removed and acrylic acid of different grades can be provided very flexibly, as required.

We have found that this object is achieved when crude acrylic acid obtained by catalytic gas phase oxidation of propene and/or acrolein, subsequent absorption into a solvent and distillation of the acrylic acid/solvent mixture is purified by fractional dynamic and static crystallization.

The present invention accordingly provides a process for preparing acrylic acid and/or esters, comprising the steps of:

(a) catalytic gas phase oxidation of propene and/or acrolein to acrylic acid to obtain a gaseous reaction product comprising acrylic acid, (b) solvent absorption of the reaction product, (c) distillation of the solvent loaded with reaction product to obtain a crude acrylic acid and the solvent, (d) purification of the crude acrylic acid by crystallization and (e) optionally esterification of the crystalline acrylic acid.

The present invention also provides an apparatus for carrying out the process of the invention. Preferred embodiments of the invention are defined in the corresponding subclaims.

Step (a)

According to the invention, the catalytic gas phase reaction of propene and/or acrolein with molecular oxygen to form acrylic acid can be effected according to known processes, especially as described in the above-cited references. The reaction is preferably carried out at from 200° to 400° C. The heterogeneous catalysts used are preferably oxidic multicomponent catalysts based on oxides of molybdenum, chromium, vanadium and/or tellurium.

The conversion of propen to acrylic acid is strongly exothermic. The reaction gas, which in addition to the starting materials and products advantageously comprises a diluting gas, for example recycle gas (see below), atmospheric nitrogen and/or water vapor, can therefore absorb only a small part of the heat of the reaction. Although the nature of the reactors used is in principle not subject to any restriction, it is most common to use tube bundle heat exchangers packed with the oxidation catalyst, since with this type of equipment the part of the heat produced in the reaction can be removed to the cooled tube walls by convection and radiation.

However, step (a) affords not pure acrylic acid, but a gaseous mixture which in addition to acrylic acid can substantially include as cocomponents unconverted acrolein and/or propene, water vapor, carbon monoxide, carbon dioxide, nitrogen, oxygen, acetic acid, propionic acid, formaldehyde, further aldehydes and maleic anhydride. The reaction product mixture customarily comprises, in each case based on the total reaction mixture, from 0.05 to 1% by weight of propene and from 0.05 to 1% by weight of acrolein, from 0.01 to 2% by weight of propane, from 1 to 20% by weight of water vapor, from 0.05 to 15% by weight of carbon oxides, from 10 to 90% by weight of nitrogen, from 0.05 to 5% by weight of oxygen, from 0.05 to 2% by weight of acetic acid, from 0.01 to 2% by weight of propionic acid, from 0.05 to 1% by weight of formaldehyde, from 0.05 to 2% by weight of aldehydes and also from 0.01 to 0.5% by weight of maleic anhydride.

Step (b)

Step (b) comprises removing the acrylic acid and part of the cocomponents from the reaction gas absorption with a solvent. According to the invention, suitable solvents include in particular all high boiling solvents, preferably solvents having a boiling point above 160° C. Of particular suitability is a mixture of diphenyl ether and biphenyl, especially the commercially available mixture of 75% by weight diphenyl ether and 25% by weight biphenyl.

Herein the terms high boilers, medium boilers and low boilers and the corresponding adjectives high boiling, medium boiling and low boiling designate, respectively, compounds with a higher boiling point than acrylic acid (high boilers); compounds with approximately the same boiling point as acrylic acid (medium boilers); and compounds with a lower boiling point than acrylic acid (low boilers).

Advantageously, the hot reaction gas obtained from step (a) is cooled down ahead of the absorption by partly evaporating the solvent in a suitable apparatus, for example a direct condenser or quench apparatus. Equipment suitable for this purpose includes venturi washers, bubble columns or spray condensers. The high boiling cocomponents of the reaction gas of step (a) condense into the unvaporized solvent. In addition, the partial evaporation of the solvent is a cleaning step for the solvent. In a preferred embodiment of the invention, a bleed stream of the unvaporized solvent, preferably from 1 to 10% of the mass flow into the absorption column, is withdrawn and subjected to a solvent cleaning step. This involves distilling the solvent over to leave a residue comprising the high boiling cocomponents which, if necessary further thickened, can be disposed of, for example incinerated. This solvent distillation serves to avoid an excessively high concentration of heavy boilers in the solvent stream.

The absorption takes place in a countercurrent absorption column which is preferably equipped with valve or dual flow plates and subjected to a downflow of (unvaporized) solvent. The gaseous reaction product and any vaporized solvent are introduced at the base of the column and then cooled down to absorption temperature. The cooling is advantageously effected by cooling cycles; that is, hot solvent is withdrawn from the column, cooled down in heat exchangers and reintroduced into the column at a point above its point of withdrawal. Besides acrylic acid, these solvent cooling cycles will condense low, high and medium boiling cocomponents and also vaporized solvent. As soon as the reaction gas stream has been cooled down to the absorption temperature, the actual absorption takes place, absorbing the rest of the acrylic acid remaining in the reaction gas and also part of the low boiling cocomponents.

The remaining, unabsorbed reaction gas of step (a) is further cooled down in order that the condensable part of the low boiling cocomponents thereof, especially water, formaldehyde and acetic acid, may be separated off by condensation. Hereinafter this condensate will be known as acid water. The remaining gas stream, hereinafter called recycle gas, consists predominantly of nitrogen, carbon oxides and unconverted starting materials. Preferably, the recycle gas is partly recirculated into the reaction stages as diluting gas.

A solvent stream loaded with acrylic acid, high and medium boiling cocomponents and also a small proportion of low boiling cocomponents is withdrawn from the base of the column used in step (b) and, in a preferred embodiment of the invention, subjected to a desorption. Advantageously, this desorption is carried out in a column, which is preferably equipped with valve or dual flow plates but can also be equipped with dumped or ordered packing, in the presence of a stripping gas. The stripping gas used can be any inert gas or gas mixture; preference is given to using a gas mixture of air and nitrogen or recycle gas, since the latter is obtained in step (a) in the course of part of the solvent being vaporized. In the desorption step, part of the recycled gas withdrawn ahead of step (a) strips the loaded solvent of the bulk of the low boilers. Since major quantities of acrylic acid are stripped out as well in the course of the desorption step, it makes economic sense not to discard this stream, hereinafter called strip recycle gas, but to recirculate it, for example into the stage where the partial vaporization of the solvent takes place, or into the absorption column. Since the stripping gas is part of the recycle gas, it still contains significant amounts of low boilers. The performance of the desorption column can be enhanced by removing the low boilers from the stripping gas before it is introduced into the column. Technically this is advantageously done by cleaning up the stripping gas in a countercurrent wash column with the solvent recovered in step (c) described below.

A solvent stream loaded with acrylic acid and virtually free of low boilers can then be withdrawn from the base of the desorption column.

Step (c)

In step (c), acrylic acid is separated from the solvent together with the medium boiling components and the last rest of low boiling cocomponents by distillation, for which in principle any distillation column can be used. Preference is given to using a column having sieve plates, for example dual flow plates or cross-flow sieve plates made of metal. In the rectifying section of the column, the acrylic acid is distilled free of the solvent and the medium boiling cocomponents, such as maleic anhydride. To reduce the low boilers content of the acrylic acid, it is advantageous to lengthen the rectifying section of the column and to withdraw the acrylic acid from the column as a sidestream. This acrylic acid will in what follows be called crude acrylic acid, regardless of its purity.

At the top of the column, a stream rich in low boilers is then withdrawn following a partial condensation. Since, however, this stream still contains acrylic acid, it is advantageously not discarded, but recycled into the absorption step (b).

At the base of the column the solvent, which is free of low boilers and almost free of acrylic acid, is withdrawn and preferably predominantly recycled into the countercurrent wash column, where the stripping gas of step (b) is cleaned up, in order that the low boilers may be washed out of the stripping gas. The almost acrylic-acid-free solvent is then fed to the absorption column.

In a preferred embodiment of the invention, the acid water, which may still contain acrylic acid in solution, is extractively treated with a small stream of the almost acrylic-acid-free solvent. In this acid water extraction, part of the acrylic acid is extracted into the solvent and thus recovered from the acid water. In return, the acid water extracts the polar medium boiling components from the solvent stream and hence avoids a buildup of these components in the solvent cycle. The resulting acid water stream of low and medium boilers may be concentrated, which is required in particular where environmental protection requirements exist. This makes it possible to meet even the tough requirements of U.S. hazardous waste law.

The crude acrylic acid obtained in step (c) comprises, in each case based on the crude acrylic acid, preferably from 98 to 99.8% by weight, particularly from 98.5 to 99.5% by weight, of acrylic acid and from 0.2 to 2% by weight, in particular from 0.5 to 1.5% by weight, of impurities, such as, for example, acetic acid, aldehydes and maleic anhydride. This acrylic acid may if desired be used for esterification, when purity requirements are not very high.

Step (d)

In step (d) the crude acrylic acid from step (c) is further purified by crystallization, preferably by means of fractional crystallization by a combination of dynamic and static crystallization. The type of dynamic or static crystallization used is not subject to any special restriction.

In static crystallization (for example U.S. Pat. No. 3,597,164 and FR 2 668 946) the liquid phase is moved only by free convection, whereas in dynamic crystallization the liquid phase is moved by forced convection. The latter can take the form of a forced flow in fully filled apparatus (cf. DE 26 06 364) or the application of a trickle or falling film to a cooled wall (DT 1 769 123 and EP 218 545).

According to the invention, preferably the crude acrylic acid to be purified is introduced into the crystallizer in liquid phase and then a solid phase which differs in composition from the liquid phase introduced is frozen out at the cooled surfaces. Once a certain proportion of the acrylic acid used has been frozen out (advantageously within the range from 50 to 80%, especially 60–70%), the remaining liquid phase is separated off. This is advantageously done by pumping e residual phase away or allowing it to flow away. The crystallization step can be followed by further purification steps such as the so-called washing of the crystal layer (cf. DE 3 708 709) or the so-called sweating, i.e. a partial melting-off of contaminated crystal areas. Advantageously, the crystallization step is followed by a sweating step when the overall purifying effect of a step is to be improved.

Dynamic and static crystallization can each be carried out in one or more stages. Multistage processes here are advantageously operated according to the countercurrent flow principle whereby, following the crystallization in each stage, the crystalline product is separated from the residue and fed to whichever is the stage with the next highest degree of purity, whereas the crystallization residue is fed to whichever stage has the next lowest degree of purity. Customarily, all stages which produce a crystalline product which is purer than the crude acrylic acid solution feed are called purifying stages while all other stages are called stripping stages.

Advantageously, a plurality of stages are operated in sequence in the same crystallizer by intermediately storing the individual stagewise fractions (crystallization product and residual melt or crystallization residue) in containers. To minimize product losses, a high crystallization yield is sought. However, the maximum yield obtainable is limited by the position of the eutectic points between acrylic acid and its cocomponents. If a eutectic composition is reached during the crystallization, no further separation takes place between acrylic acid and the corresponding impurity/cocomponent. Crystallization trials with acrylic acid of differing purity showed that even at impurity concentrations below the eutectic composition a dynamic crystallization will only produce poorly adherent crystal layers. It is therefore proposed that the dynamic crystallization residual melt be further worked up in a static crystallization, as described in EP 0 616 998. Because of the very slow layer formation, static crystallization will produce good layer adhesion coupled with a good purifying effect. The static stages are integrated into the overall process in accordance with the above-described countercurrent flow principle; that is, the static crystallization product of highest purity is fed to the stage where the dynamic crystallization product of lowest purity is produced, and the dynamic crystallization residual melt of lowest purity is fed to the stage where the purest crystals are produced by static crystallization.

Advantageously, the dynamic crystallization is carried out in a fully filled apparatus or by means of a falling or trickle film. These two methods are particularly quick and efficient. The number of crystallization stages required depends on the degree of purity desired and is readily determinable. Advantageously, a seed layer is frozen prior to the start of the crystallization.

Step (e)

If desired, the pure acrylic acid obtained in step (d) is esterified according to known methods.

The process and an apparatus are described with reference to the drawing, which illustrates a preferred embodiment of the invention.

In the drawing

Figure 1:
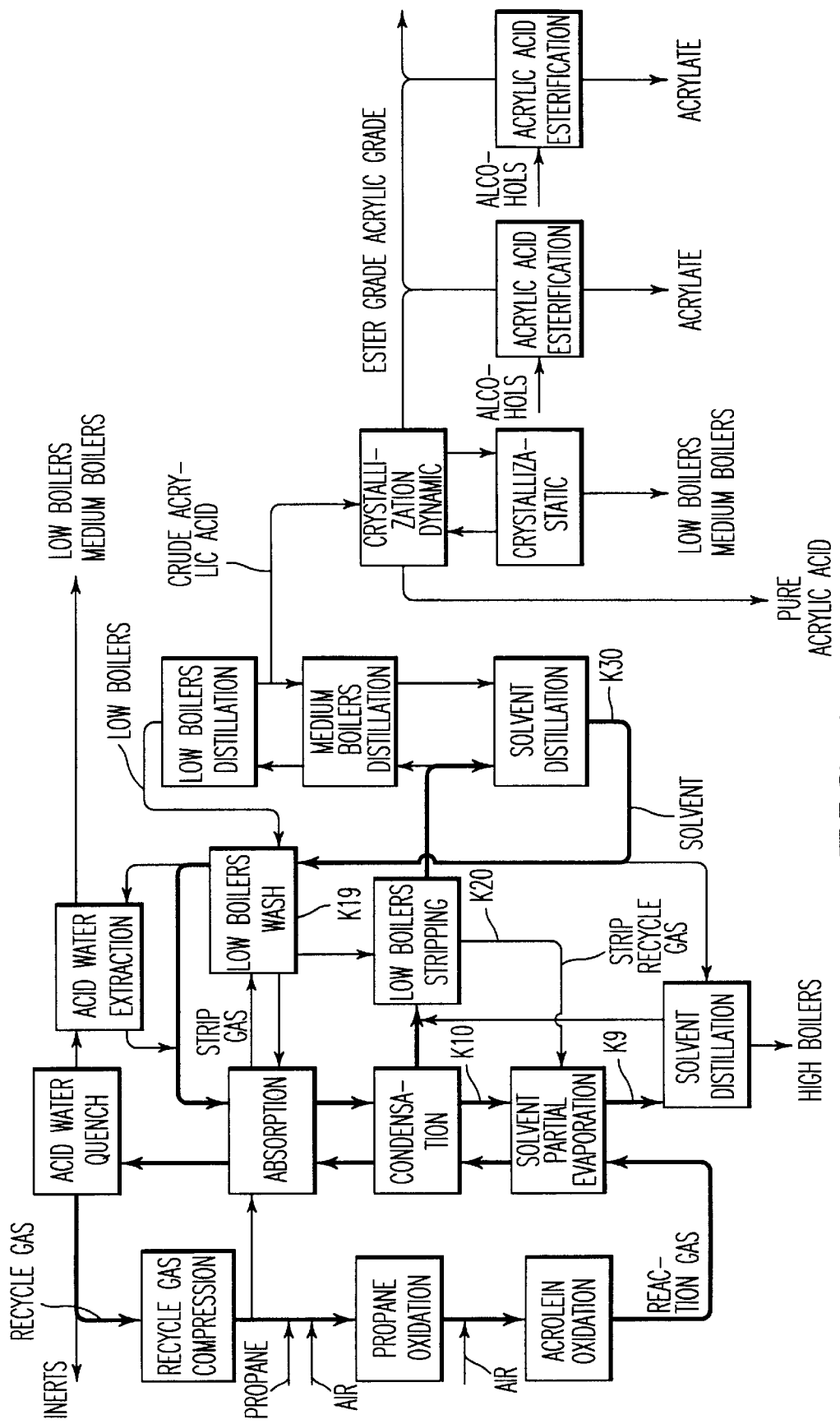
FIG. 1 shows a block diagram of the process according to the present invention.

Referring to FIG. 1, the recycle gas, which consists essentially of nitrogen, carbon oxides and unconverted staring materials, is compressed and fed together with propene and air into a reactor where the heterogeneously catalyzed oxidation of propene to acrolein takes place. The resulting intermediate reaction gas is supplied with further air in order that the heterogeneously catalyzed oxidation of acrolein may be carried out in the second reactor.

The resulting hot gaseous reaction product comprising acrylic acid is cooled down ahead of the absorption step by partial evaporation of the solvent in a direct condenser K9, the high boiling cocomponents of the reaction product condensing into the unvaporized solvent. A bleed stream from the direct condenser K9 is subjected to a solvent distillation in which the solvent is distilled over and the high boiling cocomponents remain behind. The latter can be further thickened and disposed of, for example by incineration.

Column K10 is subjected to a downflow of (unvaporized) solvent, while the vaporized solvent and the gaseous reaction product are introduced into column K10 at the base thereof and then cooled down to absorption temperature. The cooling is effected by cooling cycles (not shown). Not only the vaporized solvent but also the acrylic acid and all high and medium boiling cocomponents condense into these cooling cycles. After the entire reaction gas stream has cooled down to the absorption temperature, the actual absorption takes place. The rest of the acrylic acid remaining in the reaction gas and also part of the low boiling cocomponents are absorbed. Then the unabsorbed, remaining reaction gas is further cooled down in order that the condensable part of the low boiling cocomponents may be separated from the gas stream shown in FIG. 1 as acid water quench. In what follows, therefore, this condensate will be referred to as acid water. The remaining gas stream, the recycle gas, can then be returned in part to the reaction steps of FIG. 1 as diluting gas.

The solvent loaded with acrylic acid and cocomponents is withdrawn from the base of column K10 and fed to the desorption column K20. There the loaded solvent is stripped by a part of the recycle gas taken from the oxidation stages of the largest part of the low boilers. Since major quantities of acrylic acid are stripped off as well, this stream is recirculated, for example back into the direct condenser K9.

To enhance the desorption performance of column K20, the low boilers present in the stripping gas are removed before introduction into column K20. Technically this is advantageously done by cleaning up the stripping gas in a countercurrent wash column K19 using recovered solvent from the below-described column K30.

In the next process step a solvent stream loaded with acrylic acid and virtually free of low boilers is withdrawn from the base of the desorption column K20 and fed into the distillation column K30, which is preferably a sieve plate column. The high boiling solvent and the medium boiling cocomponents, for example maleic anhydride, condense into the base of column K30. Since the acrylic acid withdrawn at the top of column K30 still comprises significant amounts of low boiling cocomponents, this low boiler content is advantageously reduced by further lengthening the rectifying section of column K30 and withdrawing the acrylic acid from the column as a sidestream. This acrylic acid is known as crude acrylic acid.

The light-rich stream withdrawn at the top of distillation column K30 still contains acrylic acid and is therefore advantageously recycled back into the absorption column K10.

The solvent withdrawn from the base of distillation column K30, which is free of low boilers and almost free of acrylic acid, is mostly fed into the countercurrent wash column K19 in order, as mentioned above, that the low boilers may be washed out of the stripping gas stream which leads into desorption column K20. The almost acrylic-acid-free solvent is then fed to absorption column K10. A small bleed stream of the almost acrylic-acid-free solvent from the base of distillation column K30 is used for subjecting the acid water, which still contains acrylic acid in solution, to an extractive treatment. In this acid water extraction, part of the acrylic acid is recovered from the acid water and, in the other direction, the acid water extracts all polar components from the solvent bleed stream. The resulting acid water can be prevaporized and then incinerated.

The crude acrylic acid obtained from the sidestream of distillation column K30 is then subjected to a dynamic crystallization and a static crystallization. Depending on the desired acrylic acid purity requirements, it can also be sufficient to carry out a dynamic crystallization only. The dynamic crystallization is carried out either with a fully filled tube or by means of a falling film. The number of crystallization stages varies as a function of the desired acrylic acid purity. Preferably, the dynamic crystallizer is constructed as a heat exchanger. If desired, the resulting pure acrylic acid can then be esterified with alcohols to form the desired acrylates.

The process of this invention thus offers the following advantages:
  lower yield losses through the combined use of dynamic and static crystallization;
  better acid or ester quality, since the propionic acid can be separated off by crystallization. Propionic acid would be esterified to malodorous propanates in the acrylic ester production stage and would therefore be unwelcome in the end products in any event;
  no need for the addition of a chemical reagent to remove aldehydes;
  no need for acetate distillation on further processing the acid to esters;
  lower alcohol consumption at the esterification stage.

The examples which follow illustrate preferred embodiments of the invention.

Figure 2:
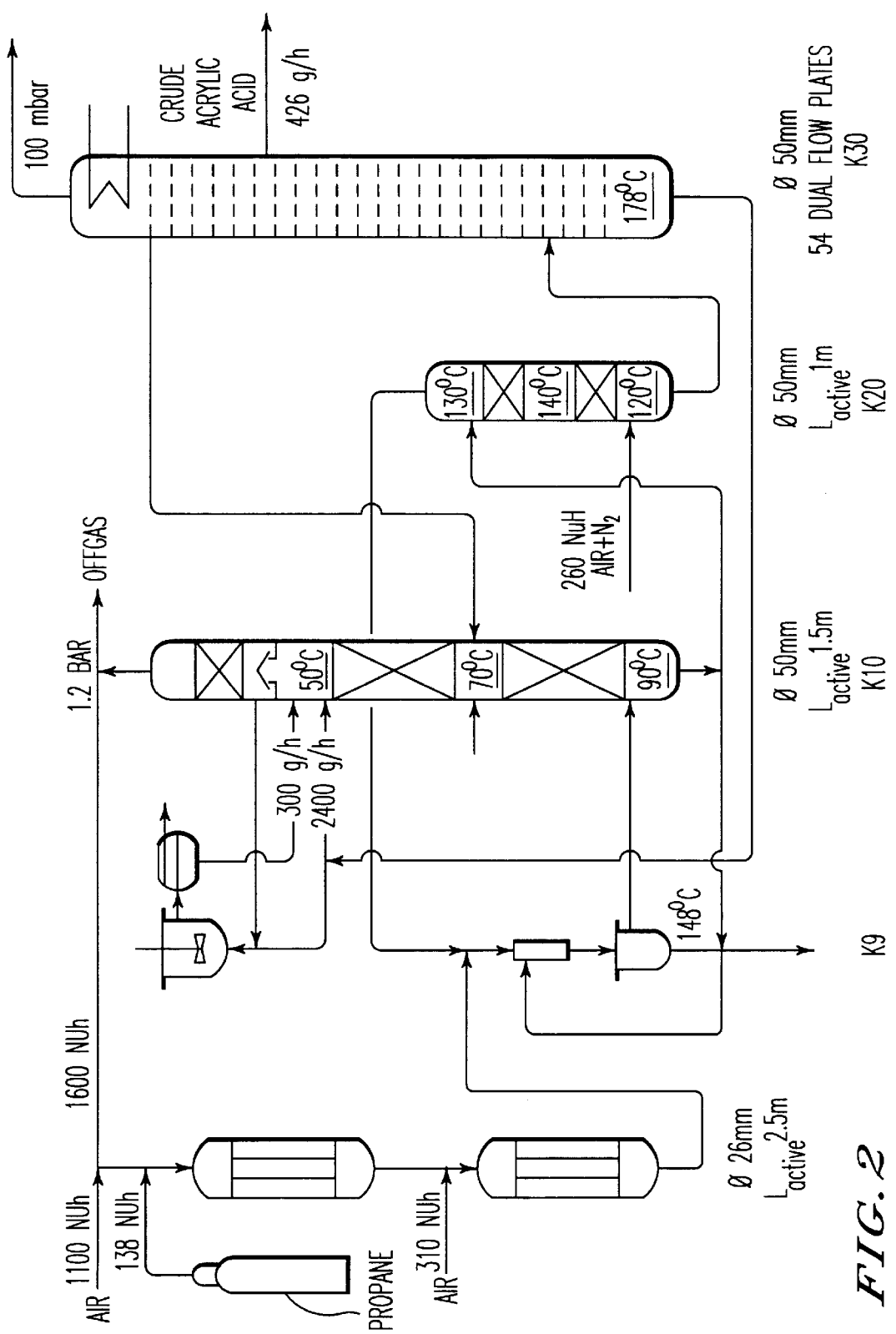
FIG. 2 shows the interconnection of the apparatus according to the present invention.

A Miniplant produced 426 g of acrylic acid per hour. The interconnection of the apparatus, the flow rates and the operating parameters employed can be seen in FIG. 2. This figure illustrates the separating steps of FIG. 1 in the form of apparatus bearing the same designations. The oxidation of propene with air via acrolein was effected in two successive reaction tubes 26 mm in diameter with a catalyst bed length of 2.5 m. The first tube was packed with a surface-impregnated catalyst as described in EP 575 897, and the second reaction tube contained a surface-impregnated catalyst as described in EP 609 750. Columns K10, K20 and K30 were mirror-finished or thermostatted laboratory columns 50 mm in diameter. The direct condenser K9 was a venturi washer. Columns K10 and K20 were packed with 5 mm metal coils. Distillation column K30 was packed with sieve plates (dual flow plates) made of metal. The perforations in the sieve plates were such that layers of froth could form.

Dynamic crystallization

The dynamic crystallization was carried out in a crystallizer as described in DE-A 26 06 364 (BASF) using a fully filled tube. The crystallizer data were as follows:
  two-pass with one tube (internal diameter 26 mm) per pass,
  tube length 5 m,
  primary-circuit pump as centrifugal pump with speed control,
  plant volume about 11 l on the primary side,
  freezeout rate about 45% (freezeout rate=mass of crystallized product/mass of crude melt),
  4 stage vessels each 100 l in volume,
  plant temperature control by refrigerating unit and 4 bar steam via heat exchanger.

The plant was controlled via a process control system, and the program sequence for one stage was as follows:
  1. Filling of primary circuit.
  2. Emptying of primary circuit and freezing out a seed layer.
  3. Raise temperature to about 2° C. below melting point.
  4. Fill primary circuit until crystallization occurs.
  5. Crystallize (temperature program).
  6. Pump down residual melt when crystallization has ended.
  7. Raise temperature to melt the crystal layer.
  8. Pump down molten crystallized product.
  9. Start of a new stage.

The temperatures, pressures, volume flows depend on the stage to be operated.

Static layer crystallization

The plant used for this purpose was a tube crystallizer made of glass with an internal diameter of 80 mm and a length of 1 m. The temperature of the crystallizer was controlled via a jacket made of glass. The fill level of the crystallizer ranged from 2.0 to 5.0 l (variable). The temperature of the plant was controlled via a programmed thermostat. The freezeout rate (after the sweating) was about 50%. The program sequence for one stage was as follows:

1. Filling the crystallizer.
2. Adjusting the temperature of the apparatus with contents to about 1K above melting temperature.
3. Crystallize (temperature program).
4. Discharge residual melt after crystallization has ended.
5. Sweating (temperature program).
6. Melt off crystallized product.
7. Start of a new stage.

The temperatures depend on the stage to be operated.

EXAMPLE 1

426 g/h of crude acrylic acid were withdrawn from the sidestream of the distillation column K30 in a quality as reported below in table 1.

EXAMPLE 2

The crude acrylic acid mentioned in Example 1 was purified in one of the above-described dynamic crystallization stages. A pure acrylic acid was obtained in a purity of 99.95% by weight with a propionic acid content of 51 weight ppm and an acetic acid content of 345 weight % ppm. The crystallization residue of tins purification stage was further worked up in three dynamic and two static crystallization stages. The purity of the pure acrylic acid obtained in this way is shown in the table below.

TABLE

| Type of acrylic acid | Acrylic acid in % by weight | Propionic acid in ppm | Acetic acid in ppm |
|---|---|---|---|
| Crude acrylic acid | 99.7 | 203 | 2000 |
| Pure acrylic acid | 99.95 | 51 | 345 |

As can be seen from the table, the combined use of dynamic and static crystallization leads to a very pure acrylic acid. More particularly, the propionic acid content (which would lead to malodorous propionates in acrylic ester production) was reduced to a quarter of its original value, which would not have been possible by distillation, even at prohibitive cost.

We claim:

1. A process for preparing acrylic acid and/or esters, comprising the steps of:
   (a) catalytic gas phase oxidation of propene and/or acrolein to acrylic acid to obtain a gaseous reaction product comprising acrylic acid,
   (b) solvent absorption of the reaction product,
   (c) distillation of the solvent loaded with reaction product in a column to obtain a crude acrylic acid and the solvent,
   (d) purification of the crude acrylic acid by crystallization and
   (e) optionally esterification of the crystalline acrylic acid.

2. A process as claimed in claim 1, wherein a high boiling solvent is used in step (b).

3. A process as claimed in claim 1 with one or more of the following features:
   the reaction product is cooled ahead of step (b) by contacting it with the solvent and evaporating part of the solvent,
   the absorption of step (b) is carried out as countercurrent absorption in an absorption column,
   the bottom product of the absorption column is subjected to a desorption ahead of step (c) to remove low boiling secondary components,
   the product obtained at the top of the distillation column in step (c) is recycled into step (b),
   the product obtained at the base of the distillation column in step (c) is recycled into the absorption step (b),
   in step (c) crude acrylic acid is removed from the distillation column as a sidestream.

4. Process as claimed in claim 3, wherein in step (d) a fractional crystallization by a combination of dynamic and static crystallization is employed.

5. A process as claimed in claim 4, wherein, in step (d), the dynamic crystallization residue is subjected to a static crystallization and the static crystallization product is subjected to dynamic crystallization.

6. A process as claimed in claim 5, wherein the dynamic crystallization is carried out with a full flow apparatus or by means of a falling film.

7. A process as claimed in claim 4, wherein the dynamic and/or static crystallizations of step (d) are carried out as countercurrent crystallizations.

* * * * *